(12) United States Patent
Lofas et al.

(10) Patent No.: US 9,470,683 B2
(45) Date of Patent: Oct. 18, 2016

(54) METHOD FOR DETERMINATION OF AGGREGATES

(75) Inventors: Stefan Lofas, Uppsala (SE); Bjorn Persson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 1120 days.

(21) Appl. No.: 13/575,197

(22) PCT Filed: Jan. 27, 2011

(86) PCT No.: PCT/SE2011/050087
§ 371 (c)(1),
(2), (4) Date: Jul. 25, 2012

(87) PCT Pub. No.: WO2011/093782
PCT Pub. Date: Aug. 4, 2011

(65) Prior Publication Data
US 2012/0295369 A1 Nov. 22, 2012

(30) Foreign Application Priority Data
Jan. 29, 2010 (SE) .................... 1050093-2

(51) Int. Cl.
G01N 33/543 (2006.01)
G01N 33/68 (2006.01)

(52) U.S. Cl.
CPC .... G01N 33/54373 (2013.01); G01N 33/6854 (2013.01)

(58) Field of Classification Search
None
See application file for complete search history.

(56) References Cited

U.S. PATENT DOCUMENTS

2009/0130105 A1* 5/2009 Glaser et al. ............ 424/136.1
2009/0288479 A1* 11/2009 Woody et al. .............. 73/105

FOREIGN PATENT DOCUMENTS

| WO | 97/09618 | 3/1997 | |
|---|---|---|---|
| WO | 2004/040317 | 5/2004 | |
| WO | 2004/109284 | 12/2004 | |
| WO | WO 2008/114003 | * 9/2008 | .......... G01N 33/543 |
| WO | 2009041543 | 4/2009 | |
| WO | 2011/049530 | 4/2011 | |

OTHER PUBLICATIONS

Jung (2000) Langmuir 16:9421-9432.*
Knowles, T., et al., Nanotechnology, 19 (2008) 384007, 1-5.
EP 11737368.8 Search Report Dated May 31, 2013.

* cited by examiner

Primary Examiner — Mark Shibuya
Assistant Examiner — Richard Moerschell
(74) Attorney, Agent, or Firm — Sutherland Asbill & Brennan LLP

(57) ABSTRACT

A method of determining aggregates of a macromolecule monomer in a fluid containing the macromolecule, comprises the steps of:
contacting a sample of the fluid with a sensing surface of an interaction analysis sensor, wherein the sensing surface is capable of specific binding interaction with the macromolecule,
determining at least one kinetic parameter for the interaction of the fluid sample with the sensing surface,
comparing the determined kinetic parameter or parameters with that or those determined for at least one fluid sample having a known fraction or fractions of aggregates of the macromolecule, and
determining therefrom the fraction of macromolecule in the sample that is in the form of aggregate or aggregates.

12 Claims, 3 Drawing Sheets

METHOD FOR DETERMINATION OF AGGREGATES

CROSS-REFERENCE TO RELATED APPLICATIONS

This application is a filing under 35 U.S.C. 371 of international application number PCT/SE2011/050087, filed Jan. 27, 2011, published on Aug. 4, 2011 as WO 2011/093782, which claims priority to application number 1050093-2 filed in Sweden on Jan. 29, 2010.

FIELD OF THE INVENTION

The present invention relates a method for determining the content of aggregates, such as dimers or trimers, of a macromolecule in a sample. The invention also relates to the use of the method in the purification of macromolecules.

BACKGROUND OF THE INVENTION

Bio-macromolecules, such as proteins, nucleic acids and polysaccharides, may often partially occur in the form of aggregates, or multimers, such as dimers, trimers or higher oligomers or aggregates. In, for example, recombinant DNA technology, where desired polypeptides or proteins are produced in host organisms and isolated from cell extracts under conditions and in concentrations quite different from those in their natural environment, the conditions may favour the formation of such aggregates through intermolecular disulphide linkages or other covalent bonds, or through non-covalent interactions.

The presence of such aggregates of a target macromolecule are many times undesired. Protein aggregation is thus a common issue encountered during bioprocess development and manufacturing of biotherapeutics. Since the multimeric forms of the macromolecule may have lower or lack the biologic activity, or even cause undesired side-effects, it is essential for therapeutic safety that the therapeutic protein is in a monomeric state and that there are no aggregates of molecules present. It is consequently of importance that the amount of aggregates produced during cell culturing and the purification process can be controlled by the implementation of appropriate measures.

The analysis of aggregates in this context is today mainly performed by size-exclusion chromatography, sometimes coupled with light scattering detection. This method is relatively slow and complex to perform and therefore not readily amenable for screening purposes with demand for larger sample volumes.

WO 2004/040317 A1 discloses a sensor device and method for determining the extent of aggregation of a protein, such as beta-amyloid, in fluid, e.g. a bodily fluid. The sensor device has a sensing layer provided with a binding partner to the protein and is sensitive to changes in the localised environment of the sensing layer caused by the introduction of the fluid. The response is typically related to changes in volume and mass from which changes in molecular density are calculated. The extent of aggregation of the protein is directly related to a change in molecular density, lowly aggregated protein giving rise to a significant increase in molecular density, and specific binding of highly aggregated protein giving rise to a less significant increase or a decrease in molecular density. The sensor device is particularly an interferometric type waveguide structure (interrogated by electromagnetic radiation in TE mode and TM mode), but also a piezoelectric sensing system, or a surface plasmon resonance device in combination with ellipsometry are suggested as sensor devices.

It is an object of the present invention to provide an improved and simplified method for assessing the content of aggregates in a fluid containing the macromolecule, especially an antibody preparation.

SUMMARY OF THE INVENTION

The present invention is based on the finding that when monomers and aggregates of a macromolecule, such as an antibody, bind to a sensor surface having a binding partner to the macromolecule immobilized thereon, the behaviour in binding reflects different kinetics between the monomers and aggregates. By studying or monitoring the kinetics for the interaction of a sample containing the macromolecule with the kinetics for a sample with a known fraction of aggregates, the content or fraction of aggregates in the sample may be assessed or determined.

In one aspect, the present invention therefore provides a method of determining aggregates of a macromolecule monomer in a fluid containing the macromolecule, comprising the steps of:
(i) contacting a sample of the fluid with a sensing surface of an interaction analysis sensor, wherein the sensing surface is capable of specific binding interaction with the macromolecule,
(ii) determining at least one kinetic parameter, or characteristic, for the interaction of the fluid sample with the sensing surface,
(iii) comparing the determined kinetic parameter or parameters with that or those determined for at least one fluid sample having a known fraction or fractions of aggregates of the macromolecule, and
(iv) determining therefrom the fraction of macromolecule in the sample that is in the form of aggregate or aggregates.

The kinetic parameter or characteristic is preferably one, or optionally both, of the on-rate and the off-rate, or a variable related thereto. The on-rate is preferably the initial on-rate.

The fluid sample with a known fraction or fractions of aggregates may, for example, be a fluid sample containing the macromolecule in monomeric form only, or two or more fluid samples with different fractions of aggregates. Preferably, a calibration curve or similar is provided which relates aggregate fraction to kinetic behaviour.

The macromolecule is preferably a protein or a polypeptide, especially an antibody.

In a currently preferred embodiment, the kinetic parameter or parameters are related to dissociation of bound macromolecule from the sensor surface.

The interaction analysis sensor is preferably a biosensor, especially a mass-sensing biosensor.

In one embodiment, the method is performed without mass transfer limitation.

In another embodiment, the method is performed with mass transfer limitation.

Further preferred embodiments of this aspect of the invention are set forth in the dependent claims.

In another aspect, the present invention provides the use of the method in optimizing the purification of a macromolecule.

A more complete understanding of the present invention, as well as further features and advantages thereof, will be

DETAILED DESCRIPTION OF THE INVENTION

Figure 1:
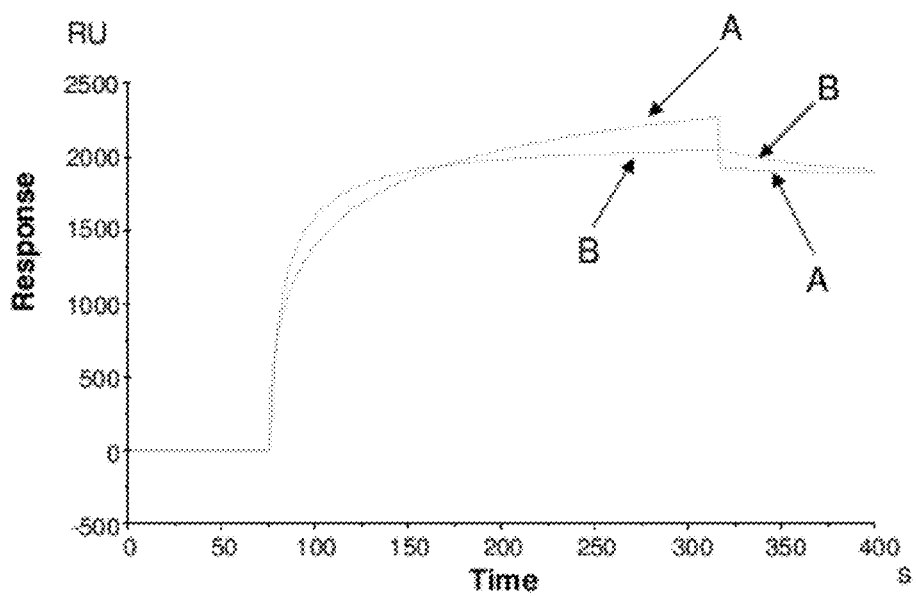
FIG. 1 is an overlay plot of two sensorgrams obtained for IgG monomer and IgG aggregate, respectively, injected on a sensor chip with immobilized Protein A. The top curve is 100% aggregate, and the bottom curve is 100% monomer.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

As mentioned above, the present invention relates to the detection and analysis of multimeric forms, or aggregates, of a macromolecule, typically a protein, such as an antibody, in a fluid sample. In brief, the method is based on utilizing differences in kinetics between monomers and aggregates of the macromolecule in their binding interaction with a specific binding partner (ligand) immobilized on a sensing surface of a biomolecular interaction analysis sensor.

The interaction analysis sensor is typically a biosensor. As is well known, a biosensor is typically based on label-free techniques, detecting a change in a property of a sensor surface, such as mass, refractive index or thickness of the immobilized layer. Typical biosensors for the purposes of the present invention are based on mass detection at the sensor surface and include especially optical methods and piezoelectric or acoustic wave methods. Representative sensors based on optical detection methods include those that detect mass surface concentration, such as sensors based on reflection-optical methods, including e.g. evanescent wave-based sensors, such as surface plasmon resonance (SPR) sensors; frustrated total reflection (FTR) sensors, and waveguide sensors, including e.g. reflective interference spectroscopy (RIfS) sensors. Piezoelectric and acoustic wave sensors include surface acoustic wave (SAW) and quartz crystal microbalance (QCM) sensors.

Biosensor systems based on SPR and other detection techniques are commercially available today. Exemplary such SPR-biosensors include the flow-through cell-based Biacore® systems (GE Healthcare Bio-Sciences AB, Uppsala, Sweden) and ProteOn™ XPR system (Bio-Rad Laboratories, Hercules, Calif., USA) which use surface plasmon resonance for detecting interactions between molecules in a sample and molecular structures (ligands or capturing molecules) immobilized on a sensing surface.

As sample is passed over the sensor surface, the progress of binding directly reflects the rate at which the interaction occurs. Injection of sample is usually followed by a buffer flow during which the detector response reflects the rate of dissociation of the complex on the surface. A typical output from the system is a graph or curve describing the progress of the molecular interaction with time, including an association phase part and a dissociation phase part. This binding curve, which is usually displayed on a computer screen, is often referred to as a "sensorgram".

With the Biacore® systems it is thus possible to determine in real time without the use of labeling, and often without purification of the substances involved, not only the presence and concentration of a particular molecule, or analyte, in a sample, but also additional interaction parameters, including kinetic rate constants for association (binding) and dissociation in the molecular interaction as well as the affinity for the surface interaction.

In the following, the present invention will to a large extent be described, for illustration only and no limitation, with regard to SPR-sensors of the Biacore® system type.

Now turning to the invention again, the above-mentioned different kinetics behaviour may be due to several factors. Two major ones reside in (i) the larger mass/volume of the aggregates compared to monomer, and (ii) the multiple binding sites (avidity) of an aggregate for a binding partner to (or ligand or capturing molecule for) the monomer, and manifest themselves in the association phase as well as the dissociation phase of a reversible surface binding interaction.

With regard to the association phase, the monomers and aggregates exhibit different binding rates, or "on-rates", to an immobilized binding partner on the sensor surface. The on-rate may be determined as the initial binding rate, represented by the initial slope of the binding curve. The slope is typically determined during a small time window shortly (a few seconds) after association has started, and usually expressed as response units per second (RU/s).

In case of a reaction-controlled interaction at the sensing surface (i.e. in the absence of any mass transfer limitation), an aggregate will give a greater response, i.e. faster on-rate, at a mass sensing surface than a monomer. The greater the fraction of aggregate is in a monomer/aggregate sample, the greater will the initial slope be, and the more will therefore the initial slope differ from that determined for a sample containing only monomer. If the on-rate has been determined in this way for a number of samples with different fractions of aggregate, the aggregate fraction in an unknown sample may thus be determined.

In case of a diffusion-limited surface interaction on the other hand, aggregates are more affected by the mass transfer limitation than the monomer resulting in a slower on-rate. Therefore, the greater the fraction of aggregate is in a monomer/aggregate sample, the smaller will the initial slope be, and the more will the initial slope differ from that determined for a sample containing only monomer, however now in a decreasing manner.

In the dissociation phase (i.e. when the surface is no longer exposed to sample and dissociation from the surface may take place), the above-mentioned stronger binding of aggregates to the surface compared to a monomer due to the aggregate having more binding sites (avidity effect) causes a slower "off-rate" for the aggregates. This is, of course, provided that the aggregate formation (at least substantially) does not block binding sites for the immobilized binding partner. Therefore, the greater the fraction of aggregate is in a monomer/aggregate sample, the slower is the off-rate, and the more will therefore the off-rate differ from that determined for a sample containing only monomer.

The off-rate may, for example, be represented by the residual binding level (response) at a predetermined time after dissociation has been initiated. In the same way as for the initial slope above, provided that the on-rate has been determined for a number of samples with different fractions of aggregate, the aggregate fraction in an unknown sample may thus be determined.

As mentioned above, for aggregate formation, such as dimerization, to cause a slower off-rate, the aggregation should leave the binding sites for the binding partner, or ligand, on the sensing surface intact, i.e. the avidity effect should be fully pronounced. However, while this is preferred, it is also within the scope of the present invention to make use of the opposite situation, i.e. that the surface-binding sites on the macromolecule are blocked by aggregation. This would in contrast lead to the aggregate having a faster dissociation (off-rate) than the monomer, and a slower association (on-rate) than the monomer. With knowledge on the aggregation mechanism and proper selection of binding ligand on the surface, it is thus possible to control if unaffected (avidity) or blocked binding sites on the macromolecule will be obtained.

For a qualitative determination of the presence of aggregate(s) in a sample, it is, of course, sufficient to compare the determined kinetic parameter with that of a sample with 100% monomer.

For the type of measurements concerned herein it is understood that, generally, a low saturation level at the sensing surface will enable a high sample throughput, whereas higher levels will facilitate detection of low fractions of aggregates in the sample.

The macromolecule for which the presence of aggregates in a preparation of the macromolecule may be determined by the method of the present invention is typically a protein or polypeptide, particularly a therapeutic protein or polypeptide, such as an antibody, but may also be, for example, a nucleic acid.

"Antibody" as used herein means an immunoglobulin (IgG) which may be natural or partly or wholly synthetically produced and also includes active fragments, including Fab antigen-binding fragments, univalent fragments and bivalent fragments. The term also covers any protein having a binding domain which is homologous to an immunoglobulin binding domain. Such proteins can be derived from natural sources, or partly or wholly synthetically produced. Exemplary antibodies are the immunoglobulin isotypes and the Fab, Fab', F(ab') 2, scFv, Fv, dAb, and Fd fragments.

The method of the present invention for determination or assessment of the fraction of aggregate in, for example, a therapeutic antibody preparation may be used to monitor aggregate formation during process development in order to optimize procedures for attaining a high quality end product. As mentioned above, the presence of aggregates in therapeutic antibody preparations generally have a negative impact on patient safety and must be effectively controlled during process manufacturing.

In the following Example, experiments demonstrating the kinetic behaviour of samples containing different fractions of antibody monomer and aggregates thereof (including 100% monomer and 100% aggregate, respectively) are described.

Example

Instrumentation

A Biacore® T100 instrument (GE Healthcare Bio-Sciences AB, Uppsala, Sweden) was used. In this instrument, a micro-fluidic system passes samples and running buffer through four individually detected flow cells (one by one or in series). As sensor chip was used Series S sensor Chip CM5 (GE Healthcare Bio-Sciences AB) which has a gold-coated surface with a covalently carboxymethyl-modified dextran polymer hydrogel. For calculations, the instrument dedicated BIAevaluation software (GE Healthcare Bio-Sciences AB, Uppsala, Sweden) was used.

The output from the instrument is a "sensorgram" which is a plot of detector response (measured in "resonance units", RU) as a function of time. An increase of 1000 RU corresponds to an increase of mass on the sensor surface of approximately 1 ng/mm$^2$.

Antibody

The antibody was a therapeutic IgG antibody (obtained from an in-house source) which contained monomers and a fraction of aggregates (prominently dimers).

Preparation of Samples

Monomers and aggregates of the antibody were separated by gel filtration using a Superdex™ 100 gel (GE Healthcare Bio-Sciences AB). A first set of samples was prepared which contained 100% monomer or 100% aggregates, respectively, at 200 µg/ml in HBS-EP+ buffer, pH 7.4 (GE Healthcare Bio-Sciences AB). A second set of samples was then prepared containing 600 µg/ml of 100%, 80%, 70%, 60%, 50%, 40%, 30%, 20%, 10% and 0% monomer, respectively.

Immobilization of Protein a on Sensor Chip

Protein A (GE Healthcare Bio-Sciences AB) was immobilized on the CM5 sensor chip by injecting a solution of Protein A in 10 mM socium acetate, pH 4.5, into the Biacore® T100.

EXPERIMENTS

Experiment 1

Samples containing 100% of either monomers or aggregates of the antibody at 200 µg/ml were injected for 4 minutes at a flow rate of 30 µl/min over the sensor chip with immobilized Protein A. The injection time was about 310 seconds (association phase) when dissociation was initiated by injection of running buffer. The sensorgrams ("binding curves") obtained are shown in FIG. 1 (overlay plot), the curve A being 100% aggregates and curve B 100% monomer. The association and dissociation phases are clearly visible in the sensorgrams.

As apparent from the sensorgrams, there is a clear difference in binding behaviour between the monomer and aggregates, which reflects different kinetics. The aggregates are more affected by mass transfer limitation (here due to selected antibody concentration) and therefore have a slower on-rate which is reflected by a less steep slope of the binding curve in the first part of the association phase of the binding curve. Aggregates also bind more strongly to the Protein A surface due to the avidity effect obtained by several binding sites to Protein A by the aggregated antibody molecule. This is reflected in the sensorgrams by the less steep dissociation phase for the aggregates. The binding level of the aggregates is supposed to be higher than the monomer due the greater mass of the aggregated molecules, but it is not clearly demonstrated in this experiment, the aggregate injection being far from saturating the immobilized Protein A on the sensor chip.

Experiment 2

Figure 2:
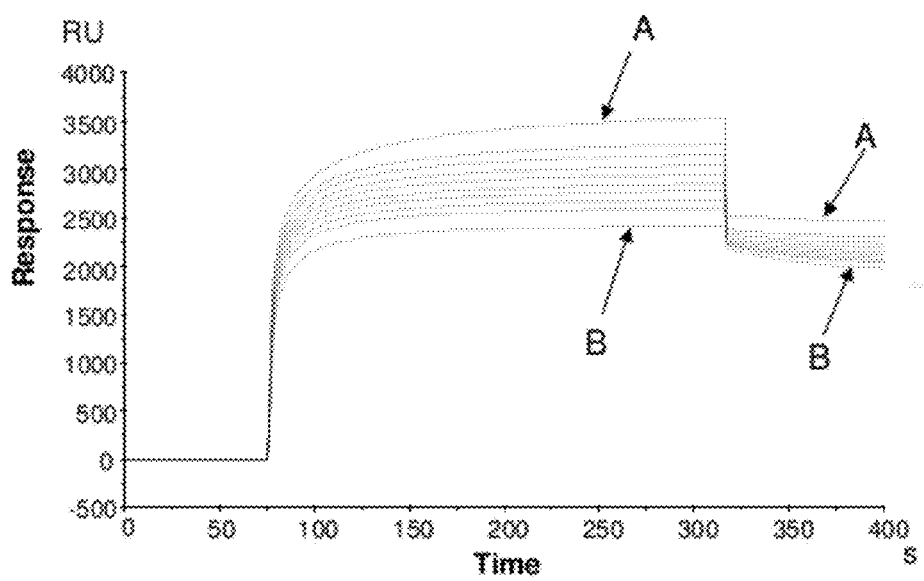
FIG. 2 is an overlay plot of ten sensorgrams for different mixtures of IgG monomers and aggregates injected on a sensor chip with immobilized Protein A. The curves represent decreasing fraction of monomer, 0% monomer for the top curve and 100% monomer for the bottom curve.

Samples containing different fractions of aggregated molecules in the range of 0 to 100% at 600 µg/ml were injected over the Protein A-coupled sensor chip. The injection time was 4 minutes and the flow rate 30 µl/min. The sensorgrams obtained are shown in FIG. 2 (overlay plot). The top curve A is 0% monomer and the bottom curve B is 100% monomer with the intermediate curves being 80%, 70%, 60%, 50%, 40%, 30%, 20%, and 10% monomer in order from top towards bottom.

Figure 3:
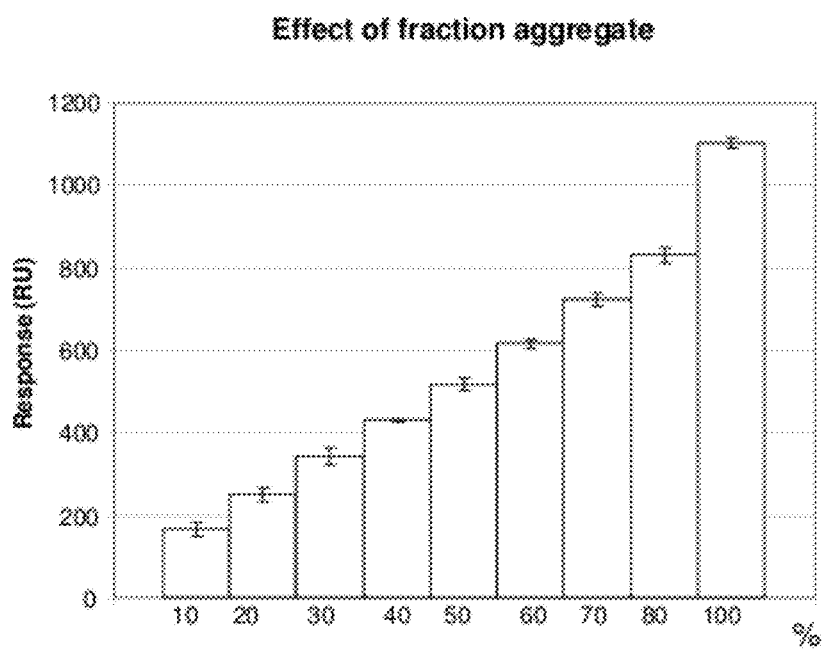
FIG. 3 is a bar chart showing the relationship between binding level (y-axis: response, RU) and dimer/monomer fraction (x-axis: %).

As apparent from the sensorgrams, there is a clear difference between the samples, with a saturation level of monomer at about 2400 RU for monomer (100% monomer sample) compared to about 3500 RU for aggregate (0% monomer sample). The differences between samples containing different fractions of monomer are demonstrated in FIG. 3 in bar chart form, the bars representing in order of increasing height (binding level) 10%, 20% 30%, 40%, 50%, 60%, 70% 80% and 100% aggregate (dimer).

To further illustrate the differences in kinetics behaviour in the association and dissociation phases between samples with different mixtures of the antibody monomer and aggregates, values from the sensorgrams above were used to determine (i) the "off-rate" in the dissociation phase at a predetermined time (94 s) after dissociation started, and (ii) the "on-rate" or "initial slope" in the association phase.

The "off-rate" is represented by the "residual level" values for the different samples at the predetermined time (94 s), and the "on-rate" is represented by the "initial slope" (or initial binding rate), which in turn here is represented by the response level measured a few second after injection started. The respective values are presented in Table 1 below.

TABLE 1

| Monomer % | Residual level (RU) | Slope (RU/s) |
|---|---|---|
| 100 | −229 | 672 |
| 80 | −203 | 755 |
| 70 | −191 | 799 |
| 60 | −172 | 842 |
| 50 | −154 | 865 |
| 40 | −138 | 892 |
| 30 | −131 | 944 |
| 20 | −106 | 946 |
| 10 | −91.9 | 1020 |
| 0 | −62.2 | 1110 |

Figure 4:
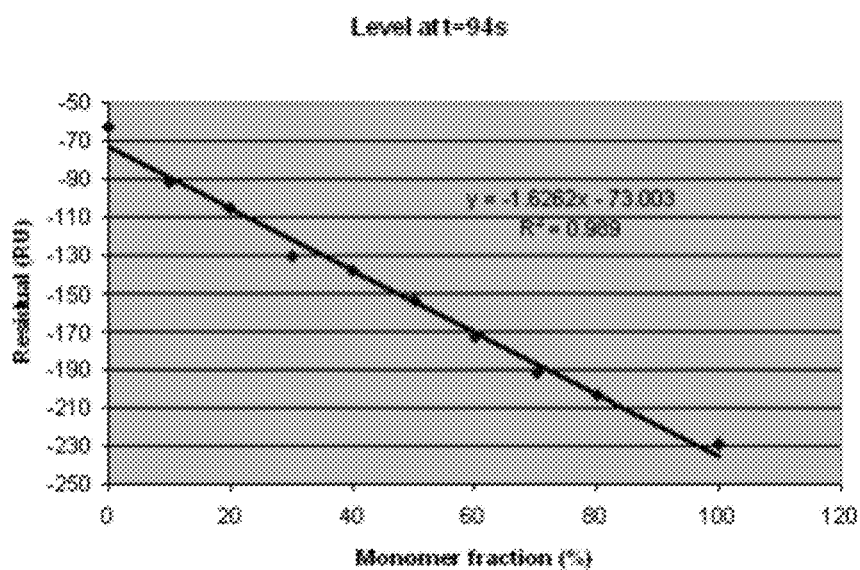
FIG. 4 is a diagram of response (y-axis: RU) vs monomer fraction (x-axis: %) for the dissociation phase of the sensorgrams in FIG. 2 at a predetermined time after dissociation is initiated.
Figure 5:
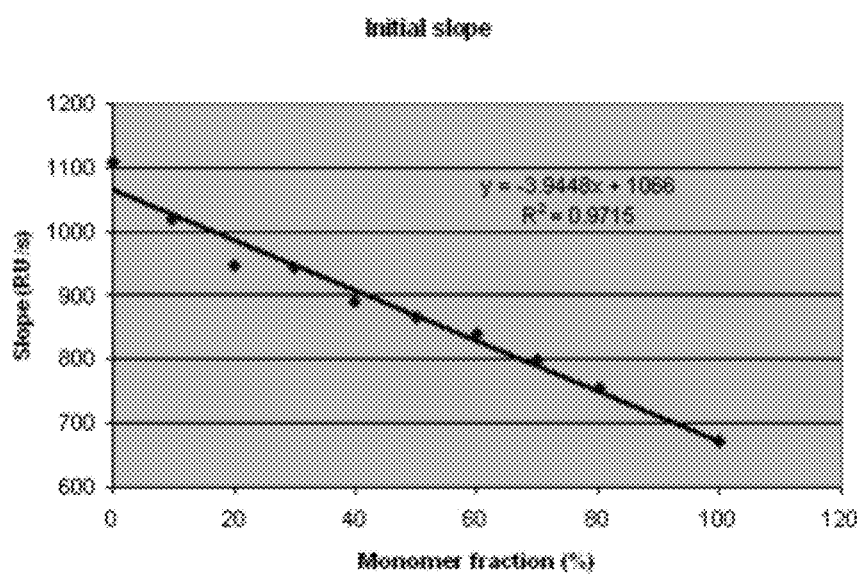
FIG. 5 is a diagram for initial slope (y-axis: RU/s) vs monomer fraction (x-axis: %) for the association phase of the sensorgrams in FIG. 2.

The % monomer vs residual level variation is shown in diagram form in FIG. 4, and the % monomer vs initial slope variation is shown in diagram form in FIG. 5. As apparent therefrom, there is a substantially linear relationship between, on the one hand, % monomer and "off-rate", and, on the other hand, % monomer and the "on-rate".

The demonstrated decreased off-rate with increased fraction of aggregate is in-line with the results in Experiment 1 above, being due to the fact that dimers have multiple binding sites for protein A and therefore bind stronger to the sensor chip than the monomer.

The on-rate, on the other hand, in contrast to the case in Experiment 1, increases with increased fraction of aggregate. This is due to the fact that with the increased antibody concentration, the surface interaction is no longer mass transfer limited, so that compared with the monomer the larger aggregate gives a higher response.

It is understood that with a capturing molecule immobilized on the sensor chip other than Protein A, with a lower affinity, the above described assessment based on the analysis of kinetic parameters would be improved.

In summary, as demonstrated in Experiments 1 and 2 above, the fraction of aggregate in an antibody-containing sample may be assessed by determining kinetics for the interaction of the sample with the sensor chip surface. Specifically, the on-rate, as determined from the association phase of the sensorgram, is proportional to the aggregate fraction when the surface interaction is reaction-controlled, and inversely proportional to the aggregate fraction when the surface interaction is diffusion-controller, i.e. at mass transfer limitation. The off-rate, on the other hand, as determined from the dissociation phase of the sensorgram, is inversely proportional to the fraction of aggregate in the sample.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method of determining aggregates of a macromolecule monomer in a fluid containing the macromolecule, comprising the steps of:
    contacting a sample of the fluid with a sensing surface of an interaction analysis sensor, wherein the sensing surface is capable of specific binding interaction with the macromolecule,
    determining at least an on-rate or an off-rate for the interaction of the fluid sample with the sensing surface,
    comparing the determined on-rate or off-rate with that determined for at least one fluid sample having a known fraction or fractions of aggregates of the macromolecule, and
    determining therefrom the fraction of macromolecule in the sample that is in the form of aggregate or aggregates.

2. The method of claim 1, comprising monitoring at least one of association and dissociation of the macromolecule to the sensing surface.

3. The method of claim 1, wherein the on-rate or off-rate is compared with the corresponding on-rate or off-rate determined for a plurality of samples containing different fractions of aggregates of the macromolecule.

4. The method of claim 1 wherein the on-rate is the initial on-rate.

5. The method of claim 1, wherein the contacting of the fluid with the sensing surface is performed under mass transfer limitation.

6. The method of claim 1, wherein the capability of the macromolecule to specifically bind to the sensing surface is at least substantially unaffected by aggregation of the macromolecule.

7. The method of claim 1, wherein the macromolecule is a protein or a polypeptide, preferably an antibody.

8. The method of claim 1, wherein the interaction analysis sensor is a biosensor.

9. The method of claim 8, wherein the biosensor is a mass-sensing biosensor, preferably a biosensor based on evanescent wave sensing, especially surface plasmon resonance (SPR).

10. The method of claim 1, wherein the sensing surface supports a ligand capable of binding antibodies.

11. The method of claim 10, wherein the ligand specifically binds to the Fc portion of antibodies.

12. The method of claim 11, wherein the ligand is Protein A or a derivate thereof.

* * * * *